US011585694B2

(12) United States Patent
Sherry

(10) Patent No.: US 11,585,694 B2
(45) Date of Patent: Feb. 21, 2023

(54) NEAR-FIELD TERAHERTZ IMAGER

(71) Applicant: TIHIVE, Meylan (FR)

(72) Inventor: Hani Sherry, Grenoble (FR)

(73) Assignee: TIHIVE, Meylan (FR)

( * ) Notice: Subject to any disclaimer, the term of this patent is extended or adjusted under 35 U.S.C. 154(b) by 0 days.

(21) Appl. No.: 17/042,843

(22) PCT Filed: Mar. 28, 2019

(86) PCT No.: PCT/FR2019/050720
§ 371 (c)(1),
(2) Date: Sep. 28, 2020

(87) PCT Pub. No.: WO2019/186074
PCT Pub. Date: Oct. 3, 2019

(65) Prior Publication Data
US 2021/0018362 A1 Jan. 21, 2021

(30) Foreign Application Priority Data

Mar. 28, 2018 (FR) ...................................... 1852688

(51) Int. Cl.
G01J 1/42 (2006.01)
G01J 1/08 (2006.01)
H01L 27/146 (2006.01)
A61B 5/0507 (2021.01)
A61B 5/00 (2006.01)

(52) U.S. Cl.
CPC ............... G01J 1/4228 (2013.01); G01J 1/08 (2013.01); H01L 27/14607 (2013.01); A61B 5/0507 (2013.01); A61B 5/444 (2013.01)

(58) Field of Classification Search
CPC .... G01J 1/4228; G01J 1/08; G01J 3/42; G01J 3/108; H01L 27/14607; H01L 27/1446; A61B 5/0507; A61B 5/444; A61B 5/4312
See application file for complete search history.

(56) References Cited

U.S. PATENT DOCUMENTS

| 9,464,933 | B1 * | 10/2016 | Sherry | ...................... G01J 1/42 |
| 2004/0069984 | A1 * | 4/2004 | Estes | ...................... B82Y 20/00 |
| | | | | 257/E23.01 |
| 2012/0212383 | A1 * | 8/2012 | Sengupta | ............. H01Q 1/2283 |
| | | | | 343/742 |

(Continued)

FOREIGN PATENT DOCUMENTS

FR 3035499 A1 10/2016

OTHER PUBLICATIONS

International Search Report in connection with International Application No. PCT/FR2019/050720 dated Aug. 23, 2019, 17 pages.

(Continued)

*Primary Examiner* — Thanh Luu
*Assistant Examiner* — Monica T Taba

(57) ABSTRACT

The invention relates to a sensor for a terahertz imaging system, comprising an array of terahertz radiation receivers; and an array of terahertz radiation transmitters having the same pitch as the array of receivers, located between the array of receivers and an analysis zone located in the near field of the transmitters, and configured such that each transmitter emits a wave towards both the analysis zone and a respective receiver of the array of receivers.

16 Claims, 1 Drawing Sheet

(56) References Cited

U.S. PATENT DOCUMENTS

2019/0318146 A1\* 10/2019 Trichopoulos ..... G06V 40/1306
2021/0057594 A1\* 2/2021 Nguyen ............. H01L 31/0392

OTHER PUBLICATIONS

Grzyb, et al., "Solid-State Terahertz Superresolution Imaging Device in 130-nm SiGe BiCMOS Technology," IEEE Transactions on Microwave Theory and Techniques, vol. 65, No. 11, Nov. 2017, 16 pages.

Pfeiffer, et al., "A 0.53 THz Reconfigurable Source Module With Up to 1 mW Radiated Power for Diffuse Illumination in Terahertz Imaging Applications," IEEE Journal of Solid-State Circuits, vol. 49, No. 12, Dec. 2014, 13 pages.

Sengupta, et al., "Silicon Integrated 280 GHz Imaging Chipset With 4x4 SiGe Receiver Array and CMOS Source," IEEE Transactions on Terahertz Science and Technology, vol. 5, No. 3, May 2015, 11 pages.

\* cited by examiner

NEAR-FIELD TERAHERTZ IMAGER

CROSS-REFERENCE TO RELATED APPLICATIONS

This application is a 371 National Stage of International Application No. PCT/FR2019/050720, filed Mar. 28, 2019, which claims priority to French Patent Application No. 1852688, filed Mar. 28, 2018, the disclosures of which are herein incorporated by reference in their entirety.

Technical Field

The invention relates to proximity imaging techniques, using in particular terahertz probes to be placed in contact with an object to be analyzed.

BACKGROUND

The terahertz (THz) wave range is between millimeter waves and visible radiation. It is accepted that the terahertz wave range extends in frequency from about 300 GHz to a few THz. Waves in this range have both radiofrequency and optical properties—in particular, they can be transmitted and received by antennas, and focused by optical systems such as silicon lenses.

THz waves have the property of passing through certain objects without the malignance of X-rays. In medical imaging, they are used, for example, to detect cancerous tissue, since such tissue has different absorption and reflection properties than healthy tissues in the THz range.

The article ["Use of a handheld terahertz pulsed imaging device to differentiate benign and malignant breast tissue", Maarten R. Grootendorst et al, Vol. 8, No. 6, 1 Jun. 2017, Biomedical Optics Express 2932] discloses a handheld probe designed to be moved over a patient's skin and analyze it by wave reflection, similar to an ultrasound probe.

THz waves are implemented in the probe via femtosecond laser pulses generated outside the probe and guided through optical fibers to a photoconductive transmitter/receiver placed inside the probe. Resulting pulses of 0.1 to 1.8 THz are then guided by an oscillating mirror between the transmitter/receiver and a quartz window present at the end of the probe, to scan 26 pixels stepwise, in an area of 15×2 mm at a frequency of 4 Hz. At each step of the scan, reflected THz pulses are returned by the corresponding pixel to the receiver.

Such a handheld probe uses complex and expensive optical technologies. In addition, the pixel pitch of about 0.6 mm provides a relatively low resolution. This resolution depends on the accuracy of the mirror drive mechanism and the relatively long wavelength of the THz waves. The 0.6 mm pixel pitch corresponds approximately to the Abbe diffraction limit in air for the lowest frequency of the pulses used, here 0.1 THz and a wavelength of 1.2 mm.

Such a system thus requires cumbersome and expensive equipment to implement an image sensor of only 15×2 mm, with the essence of the bulk being taken up by the equipment for producing the required laser beams.

Recently, THz receivers and transmitters have been successfully realized using semiconductor technologies, which are fully exploitable by electronic circuits integrated on the same chips.

THz receivers are thus grouped in an array on a semiconductor chip to form a compact image sensor. For example, the paper ["A 1 k-Pixel Video Camera for 0.7-1.1 Terahertz Imaging Applications in 65-nm CMOS", Richard Al Hadi, Hani Sherry, et al, IEEE Journal of Solid-State Circuits, VOL. 47, NO. 12, December 2012] discloses an image sensor including THz receivers produced entirely in 65-nm CMOS technology. The receivers are able to process signals at frequencies higher than the operating frequency of the transistors through the use of passive elements and configurations where the transistors are less limited in frequency (common source connections). In particular, a power sensing configuration is used—THz waves are received on an antenna and the resulting antenna signal is rectified to charge a capacitor to the peak value of the signal oscillations. Such receivers, known as homodyne receivers, do not provide phase information, but only amplitude information.

It has also been possible to design THz transmitters that are integrable in semiconductor technology, especially CMOS. One difficulty for the transmitters was to produce THz signals having a frequency higher than the operating frequency of the transistors. This difficulty was overcome by using so-called harmonic oscillators. Such an oscillator operates at a frequency compatible with the technology and produces harmonics that can be used in the THz range. U.S. Pat. No. 9,083,324 discloses such an oscillator.

Further information on integrable THz receivers and transmitters can be found in the thesis by Hani Sherry and Richard Al Hadi presented at the University of Wuppertal in 2013.

Despite the demonstrated feasibility of integrating THz components on semiconductor chips, it has not been possible to offer compact reflection sensors that could, for instance, replace the one described in the above-mentioned article of Biomedical Optics Express.

U.S. Pat. No. 9,464,933 discloses a near-field THz imager including an array of sensors. Each sensor comprises a transmission line coupled between an oscillator and a detector circuit. The oscillator generates a field that is modified by the proximity of an object to be analyzed. The modification is translated by impedance variations on the transmission line, measured by the detector circuit.

SUMMARY

A sensor for a near-field terahertz imaging system is generally provided, comprising an array of terahertz radiation receivers; and an array of terahertz radiation transmitters having the same pitch as the array of receivers, located between the array of receivers and an analysis zone located in the near field of the transmitters, and configured such that each transmitter emits a wave towards both the analysis zone and a respective receiver of the array of receivers.

The sensor may further comprise a first planar substrate of semiconductor material transparent to terahertz radiation, having an active face on which the receivers are realized in semiconductor technology; and a second planar substrate made of semiconductor material transparent to terahertz radiation, having an active face on which the transmitters are realized in semiconductor technology.

The sensor may further comprise a control circuit configured to activate in sequence each transmitter with its respective receiver.

The active face of the second substrate may face the analysis zone, and a back face of the second substrate may face the first substrate.

The active face of the first substrate may face away from the second substrate, and a back face of the first substrate may face the second substrate.

The first and second substrates may be separated from each other by a layer having a lower refractive index than the substrates.

The pitch of the arrays may be at least half the wavelength of the radiation within the substrates and each substrate may have a thickness of at most half the wavelength of the radiation within the substrate.

The receivers and transmitters may have a hexagonal configuration and be arranged in honeycomb matrices.

Each receiver and transmitter may comprise an annular antenna formed in a metal level of the active face, the average circumference of the antenna being at least half the wavelength of the terahertz radiation within the substrate; and a guard ring surrounding the antenna at the periphery of the receiver or transmitter, formed from metal patterns stacked through several levels of metal.

The guard ring may comprise metal patterns structured to form a cavity housing conductor tracks and electronic components for operating the receivers and transmitters.

BRIEF DESCRIPTION OF THE DRAWINGS

Embodiments will be set out in the following non-limiting description, in relation to the attached drawings, among which.

DESCRIPTION OF EMBODIMENTS

It is hereinafter provided to combine an array of terahertz receivers and an array of terahertz transmitters, each of which can be realized on a semiconductor chip, in a compact imager device to be applied against an object to be analyzed. The transmitters and receivers are used in near-field mode, i.e. at a sufficiently short distance, less than the wavelength, to exploit the magnetic coupling between elements.

Figure 1:
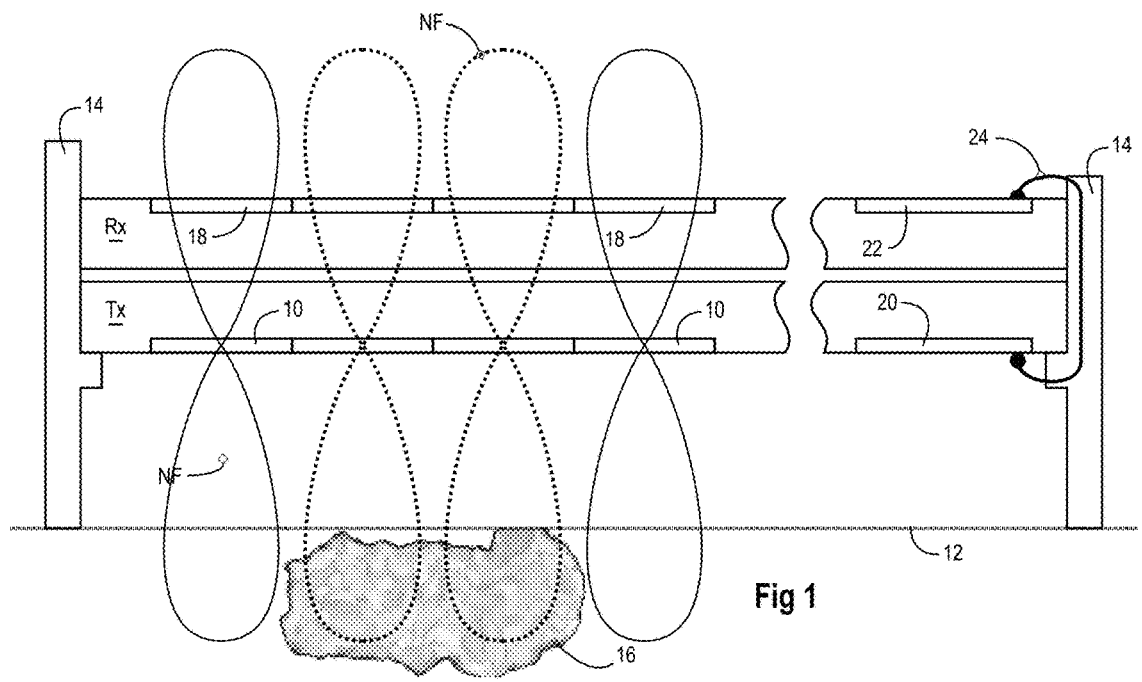
FIG. 1 is a schematic partial cross-section view of an embodiment of a compact near-field terahertz image sensor.

FIG. 1 schematically shows an imager embodiment using this principle. A substrate Tx transparent to terahertz waves comprises an array of terahertz transmitters 10. The substrate is designed to be applied against an analysis area 12, for example the skin. The substrate Tx may be in direct contact with the surface 12 or held at a given distance using a support element 14.

In this embodiment, the array of transmitter pixels 10 is located on a front face of the substrate Tx, which is turned towards zone 12. The thickness of the substrate is generally chosen to be at most half the wavelength of the radiation inside the substrate, which limits internal reflections that may disturb neighboring pixels.

The transmitter pixels in this configuration emit waves from both sides of the substrate. Thus, each transmitter presents, for each face of the substrate, a lobe characterizing the power emission as a function of the angle. The frontside lobe is smaller than the backside lobe with this configuration, meaning that the transmitter is more efficient through the back face (the transmitter is normally designed to be used through the back face).

The transmitters also have lobes that define the near-field boundaries. A power lobe defines a factor between 0 and 1, while a near-field lobe defines the spatial boundary of near-field operation. FIG. 1 shows an example of near-field lobes NF. These near-field lobes are roughly symmetrical with respect to the imager plane and have an amplitude of the order of one wavelength in air. Their exact shape, which can be determined by complex simulations, depends on the configuration of the antennas and neighboring elements.

It turns out that the nature of the elements in the near field of a terahertz transmitter can affect the characteristics of the wave, especially through the oscillator of the transmitter. Depending on the circumstances, the oscillator may be subject to a shift in impedance, phase, frequency, or amplitude. These alterations are reflected uniformly in the wave emitted from both sides of the substrate. Depending on the frequency, certain alterations or the overshooting of given thresholds may form a characteristic signature of materials or properties sought in the analyzed area, for example cancerous tissue in the skin, which can be discriminated by a higher proportion of water.

The imager of FIG. 1 is designed to use this near-field property. The distance between the substrate Tx and the measurement area 12 is chosen so that the measurement area 12 intersects the near-field lobes NF on the front face of the substrate Tx. The distance may be chosen so that the surface area of the lobes at the intersection with zone 12 is at most equal to the surface area of the transmitter pixels. This ensures the best detection coverage.

An object 16 with special properties is shown in the analysis zone in contact with the near-field lobes of the second and third transmitters. Object 16 affects the wave emitted by these transmitters, which is represented by dotted lobes.

The waves emitted on the back side by the transmitters 10 are received by respective terahertz receivers 18 arranged in an array with the same pitch as the transmitter array. The array of receivers 18 may be formed on the front face of a substrate Rx having the same characteristics as the substrate Tx. The distance between the receiver array and the transmitter array is such that the transmitters and receivers are coupled in near-field mode, if possible in such a way that each transmitter 10 is coupled to a single respective receiver 18. With this configuration, each receiver 18 measures and reproduces the properties of the wave emitted by its respective transmitter 10, including any alterations.

In practice, if the analyzed surface 12 is solid, all the emitters will be more or less disturbed in near-field mode. The imaging system may be configured generically to generate an image of the analyzed area, showing the phase, frequency and amplitude values of the waves in false colors, or to generate three separate gray scale images for each of these parameters. The parameters may be combined into a single variable with weighting coefficients to emphasize characteristic properties.

In the example in FIG. 1, the near field lobes NF have rather good properties in that they do not exceed the width of one pixel. In such a situation, it is sufficient to set the distances such that the measurement area 12 intersects the widest portions of the frontside lobes, and the receivers 18 are located in the widest portions of the backside lobes, which corresponds roughly to what is shown. This provides the best sensitivity. It is also desirable that the backside lobes pass through as much of the substrate thickness as possible, which is achieved by placing the substrates back-to-back. However, the presence between the substrates of a layer having a refractive index lower than that of the substrates (air, vacuum or other) is beneficial, because it allows the substrates to remain independent as to the thickness constraints that limit internal reflections.

Furthermore, in the example of FIG. 1, there is no possibility of crosstalk between receivers, because the backside lobe of a transmitter never overlaps several receiver pixels. There is also no possibility of crosstalk between transmitters, because the frontside lobe does not spill from one transmitter pixel to another. It is possible with this configuration to use all transmitters and receivers simultaneously as a "global shutter".

In general, especially if it is sought to reduce the pitch of the pixels, each backside lobe may spill over several receiver pixels, depending on the distance between the transmitters and receivers. For the frontside lobes, the front face can always be approached as close as desired to the analysis zone 12 to limit the useful area of the lobes to the surface of the pixels.

To avoid crosstalk problems in a general situation, each transmitter may be activated in sequence with its respective receiver. Thus, even if several neighboring receivers see an activated transmitter lobe, only the designated receiver is activated to achieve the measurement.

A sequence may be designed where several transmitters at once are activated according to a pattern where each activated transmitter does not interfere with the receivers associated with the other activated transmitters.

In FIG. 1, each substrate includes a control circuit, 20 for the transmitters and 22 for the receivers, to manage the array, in particular the pixel activation sequences. The activation of a transmitter pixel includes, among other things, turning on a local oscillator of the pixel or connecting the pixel to a shared oscillator signal. The activation of a receiver pixel includes, in particular, performing a measurement.

Since the transmitter and receiver pixels are controlled in synchronism, the signals required for synchronization may be conveyed between circuits 20 and 22 through a link 24 guided in support element 14.

The receivers may be homodyne, of very simple structure, without an oscillator, but only capable of providing an amplitude measurement. If it is desired to exploit phase or frequency information, heterodyne receivers can be used. The paper ["A Fully Integrated 320 GHz Coherent Imaging Transceiver in 130 nm SiGe BiCMOS", Chen Jiang et al, IEEE Journal of Solid-State Circuits, Vol. 51, No. 11, November 2016] as well as Hani Sherry's above-mentioned thesis describe implementations of heterodyne terahertz receivers in semiconductor technology.

Substrates Rx and Tx with their pixels and control circuits may be realized as semiconductor chips, for example in CMOS technology. Known chip-to-chip assembly techniques may be used to assemble the two substrates or chips Rx and Tx with the desired spacing.

According to an embodiment, the transmitter and receiver pixels are hexagonal and arranged in a honeycomb matrix. This hexagonal configuration of the pixels is particularly well adapted to the structure of the THz transmitters and receivers considered. Indeed, these can be based on a ring antenna, as we will see below, and the hexagonal structure is more compact than a square structure to contain a ring antenna. In addition, because the matrix is honeycombed, it can accommodate a larger number of pixels for a given pitch between pixels. These characteristics combined result in a significantly higher resolution for a given pitch than a square matrix and better rendering of oblique lines.

Figure 2:
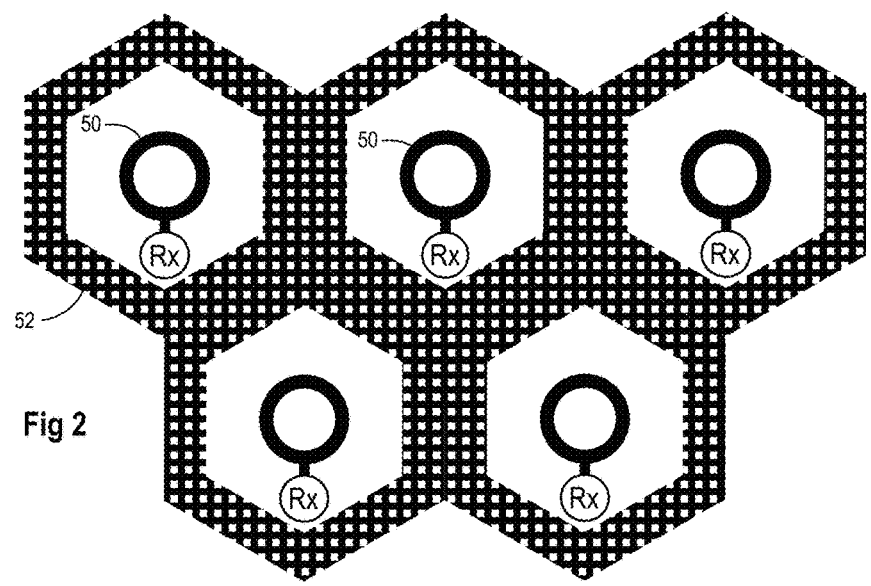
FIG. 2 represents a top view of an embodiment of hexagonal pixels realized in a semiconductor technology.

FIG. 2 represents a partial top view of an embodiment of hexagonal pixels in a matrix fabricated in a semiconductor technology, e.g. 65 nm CMOS. The matrix of receiver pixels Rx has been represented. The matrix of transmitter pixels is similar, since it is subject to the same constraints, defined by the dimensions of the antennas. The elements in this view are depicted substantially to scale for an imager designed to work at about 600 GHz, as an example. The frequency of 600 GHz corresponds to a wavelength of 0.5 mm in air. The pixels are integrated in a silicon substrate, where the wavelength decreases by a multiplication factor of about 0.6, reducing the wavelength to about 0.3 mm in silicon. Furthermore, it is acceptable to work at only half the wavelength, i.e. 0.15 mm, as this allows the resolution to be increased by a factor of 2 with an acceptable loss of gain. Thus, the antennas of the transmitters and receivers are sized to work at this wavelength. The antennas 50 here are annular, which implies that their average circumference is at least equal to the working wavelength, i.e. 0.15 mm.

The rings are etched, for example, in the last metal layer of the technology and have a width of 10 μm, i.e. an external diameter of 64 μm and an internal diameter of 54 μm.

In addition, to prevent the transverse propagation of electrical disturbances by inductive or capacitive coupling between pixels, each pixel includes a peripheral guard ring 52, which can be circular or, here, hexagonal. The antenna is centered in a predominantly metal-free area with an average diameter approximately equal to the working wavelength (0.15 mm). Thus, the inner edge of the guard ring is at least 38 μm away from the outer edge of the antenna ring. The guard ring is also 30 μm wide, and is structured to meet a metal/void ratio recommended by the technology. The pixel thus has a width of 200 μm between two opposite sides of the hexagon, a value corresponding to the pitch along each of the three axes at 0°, 120° and 240°.

Figure 3:
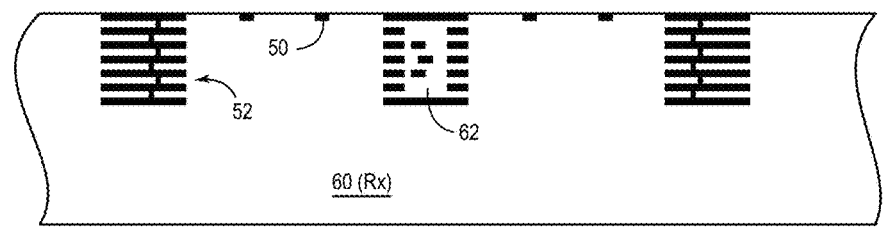
FIG. 3 is a cross-section view of an exemplary configuration of the pixels of FIG. 2.

FIG. 3 is a cross-section view of the pixels of FIG. 2. The pixels are formed on the active face of a semiconductor substrate 60, here made of silicon. The antennas 50, etched in the last metal level, are flush with the upper side of the substrate. This upper side is normally covered with a passivation layer, not shown. The guard rings 52, as shown, may be extended in depth using metal patterns stacked in all the metal levels of the technology, seven in 65 nm CMOS, interconnected by vias. The vias may be arranged around each pixel at a pitch that perfects the screening function.

To limit internal reflections, as previously mentioned, the thickness of substrate 60 is 0.15 mm.

As shown for a wall of one of the guard rings, the metal patterns can be structured to form a cavity 62. Cavity 62 may accommodate conductor tracks and electronic components for controlling the pixels. In fact, the width of two adjacent guard rings is of the order of 60 μm, which, in 65 nm technology, provides sufficient space to accommodate the majority of the conductors and electronic components required to locally exploit the pixels. This configuration reduces to a strict minimum the metallic conductors in the empty areas around the antennas, which would disturb the optical properties.

The invention claimed is:

1. A sensor for a near-field terahertz imaging system, the sensor comprising:
a first planar substrate of semiconductor material, having an active face on which an array of terahertz radiation transmitters is realized in semiconductor technology; and
a second planar substrate of semiconductor material separated from the first substrate by a layer having a lower refractive index than a refractive index of the first and second substrates, the second substrate having an active face on which an array of terahertz radiation receivers is realized in semiconductor technology, wherein each receiver is located in a near field of a respective transmitter of the first substrate.

2. The sensor according to claim 1, comprising a control circuit configured to activate in sequence each transmitter with its respective receiver.

3. The sensor according to claim 1, wherein the active face of the first substrate faces an area to be analyzed, and a back face of the first substrate faces the second substrate.

4. The sensor according to claim 3, wherein the active face of the second substrate faces away from the first substrate, and a back face of the second substrate faces the first substrate.

5. The sensor according to claim 1, wherein a pitch of the arrays is at least half a wavelength of a radiation within the substrates and each substrate has a thickness of at most half the wavelength of the radiation within the substrate.

6. The sensor according to claim 5, wherein the receivers and transmitters have a hexagonal configuration and are arranged in honeycomb matrices.

7. The sensor according to claim 6, wherein each receiver and transmitter comprises:
an annular antenna formed in a metal level of the active face, an average circumference of the antenna being at least half the wavelength of the terahertz radiation within the substrate; and
a guard ring surrounding the antenna at a periphery of the receiver or transmitter, formed from metal patterns stacked through several levels of metal.

8. The sensor according to claim 7, wherein the guard ring comprises metal patterns structured to form a cavity housing conductor tracks and electronic components for operating the receivers and transmitters.

9. A sensor for a near-field terahertz imaging system, the sensor comprising:
a first planar substrate of semiconductor material, having an active face on which an array of terahertz radiation transmitters is realized in semiconductor technology; and
a second planar substrate of semiconductor material having an active face on which an array of terahertz radiation receivers is realized in semiconductor technology, wherein each receiver is located in a near field of a respective transmitter of the first substrate;
wherein a pitch of the arrays is at least half a wavelength of a radiation within the substrates and each substrate has a thickness of at most half the wavelength of the radiation within the substrate.

10. The sensor according to claim 9, comprising a control circuit configured to activate in sequence each transmitter with its respective receiver.

11. The sensor according to claim 9, wherein the active face of the first substrate faces an area to be analyzed, and a back face of the first substrate faces the second substrate.

12. The sensor according to claim 11, wherein the active face of the second substrate faces away from the first substrate, and a back face of the second substrate faces the first substrate.

13. The sensor according to claim 9, wherein the first and second substrates are separated from each other by a layer having a lower refractive index than a refractive index of the first and second substrates.

14. The sensor according to claim 9, wherein the receivers and transmitters have a hexagonal configuration and are arranged in honeycomb matrices.

15. The sensor according to claim 14, wherein each receiver and transmitter comprises:
an annular antenna formed in a metal level of the active face, an average circumference of the antenna being at least half the wavelength of the terahertz radiation within the substrate; and
a guard ring surrounding the antenna at a periphery of the receiver or transmitter, formed from metal patterns stacked through several levels of metal.

16. The sensor according to claim 15, wherein the guard ring comprises metal patterns structured to form a cavity housing conductor tracks and electronic components for operating the receivers and transmitters.

\* \* \* \* \*